United States Patent
Luengo et al.

(10) Patent No.: US 6,720,345 B1
(45) Date of Patent: Apr. 13, 2004

(54) SEMICARBAZONE DERIVATIVES AND THEIR USE AS THROMBOPOIETIN MIMETICS

(75) Inventors: Juan I. Luengo, Audubon, PA (US); Kevin J. Duffy, Norristown, PA (US); Antony N. Shaw, Chester Springs, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/129,211

(22) PCT Filed: Nov. 3, 2000

(86) PCT No.: PCT/US00/30383

§ 371 (c)(1), (2), (4) Date: May 3, 2002

(87) PCT Pub. No.: WO01/34585

PCT Pub. Date: May 17, 2001

Related U.S. Application Data

(60) Provisional application No. 60/163,907, filed on Nov. 5, 1999.

(51) Int. Cl.[7] .................. A61K 31/425; A61K 31/415; C07D 277/04; C07D 277/18; C07D 231/04
(52) U.S. Cl. ................. 514/369; 514/404; 548/190; 548/198; 548/370.1
(58) Field of Search ................ 514/369, 404; 548/190, 198, 370.1

(56) References Cited

FOREIGN PATENT DOCUMENTS

WO       99/11262 A      3/1999

OTHER PUBLICATIONS

Beckert, R. et al., "Zur Reaktion von Derivaten des Thiosemicardazids mit Bisimidchloriden der Oxalsaure", *Monatshefte Fur Chemie*, vol. 120, No. 12, 1989, pp. 1125–1137.

Beilstein Institut zur Foerderung der Chemischen Wissenschaften, XP002159341, Beilstein Registry No. 8024644, 8029346 & Boll. Chem. Farm., ol. 137, No. 6, 1998, pp. 210–217.

Beilstein Institut zur Foerderung der Chemischen Wissenschaften, XP002159342, Beilstein Registry No. 217532, 1017055, 1598049, 4942046 & Khim. Geterotsikl. Soedin, vol. 7, 1971, pp. 1182–1185.

Beilstein Institut zur Foerderung der Chemischen Wissenschaften, XP002159343, Beilstein Registry No. 1005077 & Liet. TSR Mokslu Adad. Darb. Ser. B, 1973, pp. 95, 98.

Beilstein Institut zur Foerderung der Chemischen Wissenschaften, XP002159344, Beilstein Registry No. 865368, 1029545 & Farm. ZH (Kiev), vol. 23, No. 5, 1968, pp. 40–44.

Beilstein Institut zur Foerderung der Chemischen Wissenschaften, XP002159345, Beilstein Registry No. 1088006 & SB. Nauchn. Rab., L'Vov. Gos. Med. Inst., vol. 24, 1963, p. 22.

*Primary Examiner*—Rebecca Cook
(74) *Attorney, Agent, or Firm*—Wayne J. Dustman; Stephen Venetianer; Charles M. Kinzig

(57) ABSTRACT

Compounds of formula (I), particularly a compound of formula (Ia), are non-peptide TPO mimetics, useful in the treatment of thrombocytopenia.

11 Claims, No Drawings

SEMICARBAZONE DERIVATIVES AND THEIR USE AS THROMBOPOIETIN MIMETICS

This is a 371 of International Application PCT/US00/30383, filed Nov. 3, 2000, which claims benefit from the following Provisional Application No. 60/163,907 filed Nov. 5, 1999.

FIELD OF THE INVENTION

This invention relates to thrombopoietin (TPO) mimetics and their use as promoters of thrombopoiesis and megakaryocytopoiesis.

BACKGROUND OF THE INVENTION

Megakaryocytes are bone marrow-derived cells, which are responsible for producing circulating blood platelets. Although comprising <0.25% of the bone marrow cells in most species, they have >10 times the volume of typical marrow cells. See Kuter et al. *Proc. Natl. Acad. Aci. USA* 91:11104–11108 (1994). Megakaryocytes undergo a process known as endomitosis whereby they replicate their nuclei but fail to undergo cell division and thereby give rise to polypoid cells. In response to a decreased platelet count, the endomitotic rate increases, higher ploidy megakaryocytes are formed, and the number of megakaryocytes may increase up to 3-fold. See Harker *J. Clin. Invest.* 47:458–465 (1968). In contrast, in response to an elevated platelet count, the endomitotic rate decreases, lower ploidy megakaryocytes are formed, and the number of megakaryocytes may decrease by 50%.

The exact physiological feedback mechanism by which the mass of circulating platelets regulates the endomitrotic rate and number of bone marrow megakaryocytes is not known. The circulating thrombopoietic factor involved in mediating this feedback loop is now thought to be thrombopoietin (TPO). More specifically, TPO has been shown to be the main humoral regulator in situations involving thrombocytopenia. See, e.g., Metcalf Nature 369:519–520 (1994). TPO has been shown in several studies to increase platelet counts, increase platelet size, and increase isotope incorporation into platelets of recipient animals. Specifically, TPO is thought to affect megakaryocytopoiesis in several ways: (1) it produces increases in megakaryocyte size and number; (2) it produces an increase in DNA content, in the form of polyploidy, in megakaryocytes; (3) it increases megakaryocyte endomitosis; (4) it produces increased maturation of megakaryocytes; and (5) it produces an increase in the percentage of precursor cells, in the form of small acetylcholinesterase-positive cells, in the bone marrow.

Because platelets (thrombocytes) are necessary for blood clotting and when their numbers are very low a patient is at risk of death from catastrophic hemorrhage, TPO has potential useful application in both the diagnosis and the treatment of various hematological disorders, for example, diseases primarily due to platelet defects. Ongoing clinical trials with TPO have indicated that TPO can be administered safely to patients. In addition, recent studies have provided a basis for the projection of efficacy of TPO therapy in the treatment of thrombocytopenia, and particularly thrombocytopenia resulting from chemotherapy, radiation therapy, or bone marrow transplantation as treatment for cancer or lymphoma. See e.g., McDonald (1992) *Am. J. Ped. Hematology/Oncology* 14: 8–21 (1992).

The gene encoding TPO has been cloned and characterized. See Kuter et al., *Proc. Natl. Acad. Sci. USA* 91: 11104–11108 (1994); Barley et al., *Cell* 77: 1117–1124 (1994); Kaushansky et al., *Nature* 369:568–571 (1994); Wendling et al., *Nature* 369: 571–574 (1994); and Sauvage et al., *Nature* 369: 533–538 (1994). Thrombopoietin is a glycoprotein with two distinct regions separated by a potential Arg-Arg cleavage site. The amino-terminal region is highly conserved in man and mouse, and has some homology with erythropoietin and interferon-alpha and interferon-beta. The carboxy-terminal region shows wide species divergence.

The DNA sequences and encoded peptide sequences for human TPO receptor (TPO-R; also known as c-mpl) have been described. See, Vigon et al. *Proc. Natl. Acad. Sci. USA* 89: 5640–5644 (1992). TPO-R is a member of the haematopoietin growth factor receptor family, a family characterized by a common structural design of the extracellular domain, including for conserved C residues in the N-terminal portion and a WSXWS motif close to the transmembrane region. See Bazan *Proc. Natl. Acad. Sci. USA* 87: 6934–6938 (1990). Evidence that this receptor plays a functional role in hematopoiesis includes observations that its expression is restricted to spleen, bone marrow, or fetal liver in mice (see Souyri et al. *Cell* 63: 1137–1147 (1990)) and to megakaryocytes, platelets, and $CD34^+$ cells in humans (see Methia et al. *Blood* 82: 1395–1401 (1993)). Further evidence for TPO-R as a key regulator of megakaryopoiesis is the fact that exposure of $CD34^+$ cells to synthetic oligonucleotides antisense to TPO-R RNA significantly inhibits the appearance of megakaryocyte colonies without affecting erythroid or myeloid colony formation. Some workers postulate that the receptor functions as a homodimer, similar to the situation with the receptors for G-CSF and erythropoietin.

The slow recovery of platelet levels in patients suffering from thrombocytopenia is a serious problem, and has lent urgency to the search for a blood growth factor agonist able to accelerate platelet regeneration.

It would be desirable to provide compounds which allow for the treatment of thrombocytopenia by acting as a TPO mimetic.

As disclosed herein it has unexpectedly been discovered that certain substituted thiosemicarbazone derivatives are effective as agonists of the TPO receptor, they are potent TPO mimetics.

SUMMARY OF THE INVENTION

This invention relates to compounds of Formula (I):

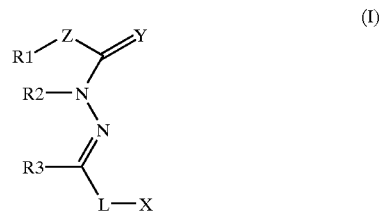

wherein:
  $R^1$ and $R^2$ are each independently selected from hydrogen, $C_{1-2}$alkyl, aryl, substituted aryl, and alkyl substituted with one or more substituents selected from the group consisting of: alkoxy, acyloxy, aryl, substituted aryl, amino, N-acylamino, oxo, hydroxy, cycloalkyl, substituted cycloalkyl, $—C(O)OR^7$, $—S(O)_2NR^7R^8$, $—S(O)_nR^6$, aryloxy, nitro, cyano, halogen, and protected —OH, where $R^6$ is selected from hydrogen, alkyl, cycloalkyl, $C_1$–$C_{12}$aryl, substituted alkyl, substituted cycloalkyl and substituted $C_1$–$C_{12}$aryl, and $R^7$ and $R^8$ are independently selected from hydrogen, cycloalkyl, aryl, substituted cycloalkyl, substituted aryl, alkyl or alkyl substituted with one or more substituents selected from the group consisting of: alkoxy, acyloxy, aryloxy, amino, N-acylamino, oxo, hydroxy, —C(O)OR$^6$, —S(O)$_n$R$^6$, —C(O)NR$^6$R$^6$, —S(O)$_2$NR$^6$R$^6$, nitro, cyano, cycloalkyl, substituted cycloalkyl, halogen, $C_1$–$C_{12}$aryl, substituted $C_1$–$C_{12}$aryl and protected —OH where $R^6$ is as described above; and n is 0–3; or $R^1$ and $R^2$ taken together with the

group to which they are attached represent a ring of formula (A):

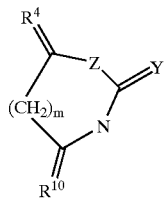

where $R^4$ and $R^{10}$ are each independently selected from two hydrogens, =NR$^5$, =O, =S, and =CHR$^5$, where $R^5$ is $C_1$–$C_{12}$aryl or substituted $C_1$–$C_{12}$aryl; and m is 0 to 2;

Z is a bond or selected from S or NR$^5$, where $R^5$ is $C_1$–$C_{12}$aryl or substituted $C_1$–$C_{12}$aryl;

$R^3$ is selected from hydrogen, $C_1$–$C_{10}$alkyl, phenyl, substituted phenyl, carboxyl or $C_1$–$C_{10}$alkoxycarbonyl;

L is a group of formula (L):

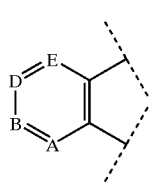

where

A, B, D and E independently represent CR$^{11}$ or N; where $R^{11}$ is selected from hydrogen, halogen, —CF$_3$, —CN, —SO$_3$H, —SO$_3$Na, —SO$_2$R$^{14}$, —NO$_2$, phenyl, substituted phenyl, $C_1$–$C_{10}$alkyl, $C_1$–$C_{10}$alkoxy, $C_1$–$C_{10}$acyloxy, arylalkoxy, —COR$^{14}$, —NR$^{12}$R$^{13}$, hydroxy or cycloalkyl; where $R^{14}$ is selected from hydroxy, $C_1$–$C_{10}$alkyl, phenyl, amino, mono- or dialkylamino;

$R^{12}$ and $R^{13}$ are independently selected from hydrogen, $C_{1-10}$alkyl, $C_1$–$C_{12}$aryl, substituted $C_1$–$C_{12}$aryl, $C_{1-10}$acyl or cycloalkyl;

or either A=B or D=E alternatively represent O, S or NR$^{12}$; where $R^{12}$ is as defined above;

Y is selected from —S, —O and —NR$^{15}$, where $R^{15}$ is selected from hydrogen, $C_1$–$C_{10}$alkyl, substituted $C_1$–$C_{10}$alkyl, $C_1$–$C_6$alkylphenyl, substituted $C_1$–$C_6$alkylphenyl, $C_1$–$C_{10}$acyl, substituted $C_1$–$C_{10}$acyl, or SO$_2$R$^9$, where $R^9$ is $C_1$–$C_{10}$alkyl, substituted $C_1$–$C_{10}$alkyl, $C_1$–$C_{12}$aryl or substituted $C_1$–$C_{12}$aryl; and X is selected from —SR$^{16}$, —OR$^{16}$ or —NHR$^{17}$; where $R^{16}$ is hydrogen, $C_1$–$C_{10}$alkyl or substituted $C_1$–$C_{10}$alkyl;

$R^{17}$ is hydrogen, $C_1$–$C_{10}$alkyl, substituted $C_1$–$C_{10}$alkyl, $C_1$–$C_6$alkylphenyl, $C_1$–$C_{10}$acyl, substituted $C_1$–$C_{10}$acyl or SO$_2$R$^9$; where $R^9$ is $C_1$–$C_{10}$alkyl, substituted $C_1$–$C_{10}$alkyl, $C_1$–$C_{12}$aryl or substituted $C_1$–$C_{12}$aryl; and pharmaceutically acceptable salts, hydrates, solvates and esters thereof, provided that:

when $R^1$ and $R^2$ do not form a ring and X is not —NHSO$_2$R$^9$, $R^5$ is not a substituted or unsubstituted pyridyl or a substituted or unsubstituted phenyl.

This invention relates to a method of treating thrombocytopenia, which comprises administering to a subject in need thereof an effective amount of a TPO mimetic compound of Formula (I).

The present invention also relates to the discovery that the compounds of Formula (I) are active as agonists of the TPO receptor.

In a further aspect of the invention there is provided novel processes and novel intermediates useful in preparing the presently invented TPO mimetic compounds.

Included in the present invention are pharmaceutical compositions comprising a pharmaceutical carrier and compounds useful in the methods of the invention.

Also included in the present invention are methods of co-administering the presently invented TPO mimetic compounds with further active ingredients.

DETAILED DESCRIPTION OF THE INVENTION

This invention relates to compounds of Formula (I) as described above.

Preferred among the presently invented Formula I compounds are those in which $R^5$ is $C_1$–$C_{12}$aryl substituted with a carboxy or sulfonic acid substituent.

Preferred among the presently invented Formula I compounds are those in which $R^1$ and $R^2$ are selected from hydrogen, $C_{1-10}$alkyl, benzyl, substituted benzyl, phenyl, substituted phenyl, or $R^1$ and $R^2$ taken together with the

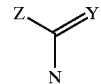

group to which they are attached represent a ring of formula (A):

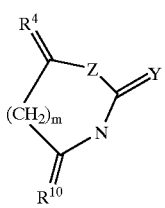

(A)

where R[4] and R[10] are each independently selected from two hydrogens, =O, or =CHR[5], where R[5] is $C_1$–$C_{12}$aryl or substituted $C_1$–$C_{12}$aryl; and m is 0 to 2.

Preferred among the presently invented Formula I compounds are those in which:

Z is S or —NR[5] where R[5] is phenyl substituted with a carboxy or sulfonic acid substituent, a six membered aromatic ring containing from 1 to 3 heteroatoms and substituted with a carboxy or sulfonic acid substituent, or a $C_1$–$C_2$alkylphenyl substituted with a carboxy or sulfonic acid substituent;

L is $C_3$–$C_6$aryl optionally substituted with form 1 to 3 substituents selected from the group consisting of: Br, Cl, $CF_3$, F, —$CH_3$ and substituted phenyl;

Y is S; and

X is —OH; and pharmaceutically acceptable salts, hydrates, solvates and esters thereof, provided that;

when R[1] and R[2] do not form a ring, R[5] is not a substituted or unsubstituted pyridyl or a substituted or unsubstituted phenyl.

Preferred among the presently invented compounds are:

3-[(2-hydroxy-3,5-dibromophen-1-yl)methyleneamino]-2-thioxothiazolidin-4-one (Compound A);

3-(3-carboxyphenyl)-1-[(1-(3,4-dimethylphenyl)-5-hydroxy-3-methyl-1H-pyrazol-4-ylmethylene)amino]-2-thioxoimidazolidin-4-one;

3-(4-carboxyphenyl)-1-[(1-(3,4-dimethylphenyl)-5-hydroxy-3-methyl-1H-pyrazol-4-ylmethylene)amino]-2-thioxoimidazolidin-4-one;

5-(4-carboxybenzylidene)-3-[(1-{3,4-dimethylphenyl}-4-hydroxy-3-methyl-1H-pyrazol-4-ylmethylene)amino]-2-thioxothiazolidin-4-one; and 5-(3-carboxybenzylidene)-3-[(1-{3,4-dimethylphenyl}-4-hydroxy-3-methyl-1H-pyrazol-4-ylmethylene)amino]-2-thioxothiazolidin-4-one.

Compounds of Formula (I) are included in the pharmaceutical compositions of the invention and used in the methods of the invention.

By the term "protected hydroxy" or "protected —OH" as used herein, is meant the alcoholic or carboxylic—OH groups which can be protected by conventional blocking groups in the art as described in "Protective Groups In Organic Synthesis" by Theodora W. Greene, Wiley-Interscience, 1981, New York. Compounds containing protected hydroxy groups may also be useful as intermediates in the preparation of the pharmaceutically active compounds of the invention.

By the term "aryl" as used herein, unless otherwise defined, is meant a cyclic or polycyclic aromatic ring containing from 1 to 14 carbon atoms and optionally containing from one to five heteroatoms, provided that when the number of carbon atoms is 1 the aromatic ring contains at least four heteroatoms, when the number of carbon atoms is 2 the aromatic ring contains at least three heteroatoms, when the number of carbons is 3 the aromatic ring contains at least two heteroatoms and when the number of carbon atoms is 4 the aromatic ring contains at least one heteroatom.

By the term "$C_1$–$C_{12}$aryl" as used herein, unless otherwise defined, is meant phenyl, naphthalene, 3,4-methylenedioxyphenyl, pyridine, biphenyl, quinoline, pyrimidine, quinazoline, thiophene, furan, pyrrole, pyrazole, imidazole and tetrazole.

By the term "$C_3$–$C_6$aryl" as used herein, unless otherwise defined, is meant a cyclic or polycyclic aromatic ring containing from 3 to 6 carbon atoms and optionally containing from one to 4 heteroatoms, provided that when the number of carbon atoms is 3 the aromatic ring contains at least two heteroatoms and when the number of carbon atoms is 4 the aromatic ring contains at least one heteroatom.

By the term "substituted" as used herein, unless otherwise defined, is meant that the subject chemical moiety has one or more substituents selected from the group consisting of: hydroxyalkyl, alkoxy, acyloxy, alkyl, aryl, amino, N-acylamino, hydroxy, —$(CH_2)_gC(O)OR^6$, —$S(O)_nR^7$, nitro, cyano, halogen, trifluoromethyl and protected —OH, where g is 0–6, R[6] is hydrogen or alkyl, n is 0–3, and R[7] is hydrogen or alkyl.

By the term "alkoxy" as used herein is meant —Oalkyl where alkyl is as described herein including —$OCH_3$ and —$OC(CH_3)_2CH_3$.

The term "cycloalkyl" as used herein unless otherwise defined, is meant a nonaromatic, unsaturated or saturated, cyclic or polycyclic $C_3$–$C_{12}$.

Examples of cycloalkyl and substituted cycloalkyl substituents as used herein include: cyclohexyl, 4-hydroxycyclohexyl, 2-ethylcyclohexyl, propyl 4-methoxycyclohexyl, 4-methoxycyclohexyl, 4-carboxycyclohexyl and cyclopentyl.

By the term "acyloxy" as used herein is meant —OC(O)alkyl where alkyl is as described herein. Examples of acyloxy substituents as used herein include: —$OC(O)CH_3$, —$OC(O)CH(CH_3)_2$ and —$OC(O)(CH_2)_3CH_3$.

By the term "N-acylamino" as used herein is meant —N(H)C(O)alkyl, where alkyl is as described herein. Examples of N-acylamino substituents as used herein include: —$N(H)C(O)CH_3$, —$N(H)C(O)CH(CH_3)_2$ and —$N(H)C(O)(CH_2)_3CH_3$.

By the term "aryloxy" as used herein is meant —$OC_6$–$C_{12}$aryl where $C_6$–$C_{12}$aryl is phenyl, naphthyl, 3,4-methylenedioxyphenyl, pyridyl or biphenyl optionally substituted with one or more substituents selected from the group consisting of: alkyl, hydroxyalkyl, alkoxy, trifuloromethyl, acyloxy, amino, N-acylamino, hydroxy, —$(CH_2)_gC(O)OR^6$, —$S(O)_nR^7$, nitro, cyano, halogen and protected —OH, where g is 0–6, R[6] is hydrogen or alkyl, n is 0–3 and R[7] is hydrogen or alkyl. Examples of aryloxy substituents as used herein include: phenoxy, 4-fluorophenyloxy and biphenyloxy.

By the term "heteroatom" as used herein is meant oxygen, nitrogen or sulfur.

By the term "halogen" as used herein is meant a substituent selected from bromide, iodide, chloride and fluoride.

By the term "alkyl" and derivatives thereof and in all carbon chains as used herein is meant a linear or branched, saturated or unsaturated hydrocarbon chain having $C_1$–$C_{12}$ carbon atoms. Examples of alkyl substituents as used herein include: —$CH_3$, —$CH_2$—$CH_3$, —$CH_2$—$CH_2$—$CH_3$, —$CH(CH_3)_2$, —$C(CH_3)_3$, —$(CH_2)_3$—$CH_3$, —$CH_2$—$CH(CH_3)_2$ and —$CH(CH_3)$—$CH_2$—$CH_3$, —$CH=CH_2$.

By the term "treating" and derivatives thereof as used herein, is meant prophylatic or therapeutic therapy.

All publications, including but not limited to patents and patent applications, cited in this specification are herein incorporated by reference as though fully set forth.

Compounds of Formula (I) are included in the pharmaceutical compositions of the invention and used in the methods of the invention. Where a —COOH or —OH group is present, pharmaceutically acceptable esters can be employed, for example methyl, ethyl, pivaloyloxymethyl, and the like for —COOH, and acetate maleate and the like for —OH, and those esters known in the art for modifying solubility or hydrolysis characteristics for use as sustained release or prodrug formulations.

The novel compounds of Formula I are prepared as shown in Scheme I below wherein $R^1$, $R^2$, $R^3$, Z, Y, L and X are as defined in Formula I and provided that these substituents do not include any such substituents that render inoperative the Scheme I process. All of the starting materials are commercially available or are readily made from commercially available starting materials by those of skill in the art.

Scheme 1

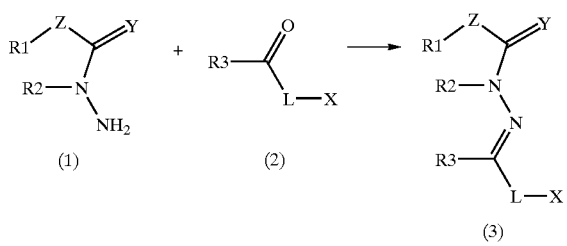

Compounds 1, are condensed with carbonyl compounds 2, available commercially or prepared by literature methods, in a suitable solvent with or without the addition of an acid catalyst such as HCl to furnish the final compound 3.

The treatment of thrombocytopenia, as described herein, is accomplished by enhancing the production of platelets.

By the term "co-administering" and derivatives thereof as used herein is meant either simultaneous administration or any manner of separate sequential administration of a TPO mimetic compound, as described herein, and a further active ingredient or ingredients, known to treat thrombocytopenia, including chemotherapy-induced thrombocytopenia and bone marrow transplantation and other conditions with depressed platelet production. Preferably, if the administration is not simultaneous, the compounds are administered in a close time proximity to each other. Furthermore, it does not matter if the compounds are administered in the same dosage form, e.g. one compound may be administered topically and another compound may be administered orally.

Because the pharmaceutically active compounds of the present invention are active as TPO mimetics they exhibit therapeutic utility in treating thrombocytopenia and other conditions with depressed platelet production.

In determining potency as TPO mimetics, the following assays were employed:

Luciferase Assay

Compounds of the present invention were tested for potency as mimetics of the TPO receptor in a Luciferase assay such as described in Lamb, et al., *Nucleic Acids Research* 23: 3283–3289 (1995) and Seidel, et al., *Proc. Natl. Acad. Sci., USA* 92: 3041–3045 (1995) by substituting a TPO-responsive BaF3 cell line (Vigon et al. *Proc. Natl. Acad. Sci. USA* 1992, 89, 5640–5644) for the HepG2 cells utilized therein. The murine BaF3 cells express TPO receptors and closely match the pattern of STAT (signal transducers and activators of transcription) activation observed in primary murine and human bone marrow cells in response to TPO.

Some of the preferred compounds of this invention were also active in an in vitro proliferation assay using the murine 32D-mpl cell line (Bartley, T. D. et al., Cell, 1994, 77, 1117–1124). 32D-mpl cells express Tpo-R and their survival is dependent on the presence of TPO.

The pharmaceutically active compounds within the scope of this invention are useful as TPO mimetics in mammals, including humans, in need thereof.

Within the scope of the invention Compound A showed activation of about 9% of control (control is the maximal response to TPO) at a concentration of 10 uM in the luciferase assay.

Some of the preferred compounds within the scope of the invention showed activation from about 0% to 9% control at a concentration of 1–10 uM in the luciferase assay. The preferred compounds of the invention also promoted the proliferation of 32D-mpl cells at a concentration of 10 to 30 uM.

The present invention therefor provides a method of treating thrombocytopenia and other conditions with depressed platelet production, which comprises administering a compound of Formula (I), and pharmaceutically acceptable salts, hydrates, solvates and esters thereof in a quantity effective to enhance platelet production. The compounds of Formula (I) also provide for a method of treating the above indicated disease states because of their demonstrated ability to act as TPO mimetics. The drug may be administered to a patient in need thereof by any conventional route of administration, including, but not limited to, intravenous, intramuscular, oral, subcutaneous, intradermal, and parenteral.

The pharmaceutically active compounds of the present invention are incorporated into convenient dosage forms such as capsules, tablets, or injectable preparations. Solid or liquid pharmaceutical carriers are employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral or parenteral products.

Doses of the presently invented pharmaceutically active compounds in a pharmaceutical dosage unit as described above will be an efficacious, nontoxic quantity preferably selected from the range of 0.001–100 mg/kg of active compound, preferably 0.001–50 mg/kg. When treating a human patient in need of a TPO mimetic, the selected dose is administered preferably from 1–6 times daily, orally or parenterally. Preferred forms of parenteral administration include topically, rectally, transdermally, by injection and continuously by infusion. Oral dosage units for human administration preferably contain from 0.05 to 3500 mg of active compound. Oral administration, which uses lower dosages is preferred. Parenteral administration, at high dosages, however, also can be used when safe and convenient for the patient.

Optimal dosages to be administered may be readily determined by those skilled in the art, and will vary with the particular TPO mimetic in use, the strength of the preparation, the mode of administration, and the advancement of the disease condition. Additional factors depending on the particular patient being treated will result in a need to adjust dosages, including patient age, weight, diet, and time of administration.

The method of this invention of inducing TPO mimetic activity in mammals, including humans, comprises administering to a subject in need of such activity an effective TPO mimetic amount of a pharmaceutically active compound of the present invention.

The invention also provides for the use of a compound of Formula (I) in the manufacture of a medicament for use as a TPO mimetic.

The invention also provides for the use of a compound of Formula (I) in the manufacture of a medicament for use in therapy.

The invention also provides for the use of a compound of Formula (I) in the manufacture of a medicament for use in enhancing platelet production.

The invention also provides for the use of a compound of Formula (I) in the manufacture of a medicament for use in treating thrombocytopenia.

The invention also provides for a pharmaceutical composition for use as a TPO mimetic which comprises a compound of Formula (I) and a pharmaceutically acceptable carrier.

The invention also provides for a pharmaceutical composition for use in the treatment of thrombocytopenia which comprises a compound of Formula (I) and a pharmaceutically acceptable carrier.

The invention also provides for a pharmaceutical composition for use in enhancing platelet production which comprises a compound of Formula (I) and a pharmaceutically acceptable carrier.

No unacceptable toxicological effects are expected when compounds of the invention are administered in accordance with the present invention.

In addition, the pharmaceutically active compounds of the present invention can be co-administered with further active ingredients, such as other compounds known to treat thrombocytopenia, including chemotherapy-induced thrombocytopenia and bone marrow transplantation and other conditions with depressed platelet production, or compounds known to have utility when used in combination with a TPO mimetic.

Without further elaboration, it is believed that one skilled in the art can, using the preceding description, utilize the present invention to its fullest extent. The following Examples are, therefore, to be construed as merely illustrative and not a limitation of the scope of the present invention in any way.

EXPERIMENTAL DETAILS

Example 1

3-[(2-hydroxy-3,5-dibromophen-1-yl) methyleneamino]-2-thioxothiazolidin-4-one

A solution of 3,5-dibromo-2-hydroxybenzaldehyde (104 mg, 0.371 mmol) in methanol (1 mL) was added to a solution of 3-aminorhodanine (50 mg, 0.337 mmol) in methanol (5 mL) and the mixture allowed to stand at room temperature. After 1 h, the precipitate was filtered, washed (methanol, ether) and dried to give the title compound (93 mg, 67%) as a pale yellow solid. LCMS m/e 409, 411, 413 [M+H]$^+$.

Example 2

3-(3-carboxyphenyl)-1-[(1-(3,4-dimethylphenyl)-5-hydroxy-3-methyl-1H-pyrazol-4-ylmethylene) amino]-2-thioxoimidazolidin-4-one a) 1-(3,4-Dimethylphenyl)-3-methyl-3-pyrazolin-5-one A solution of 3,4-dimethylphenylhydrazine (7.3 g; 0.053 mol.) and ethyl acetoacetate (6.9 g; 0.053 mol.) in glacial acetic acid (50.0 mL) was stirred and heated at 100° for 24 h. The solvent was evaporated and the product purified by chromatography (silica gel, 50% ethyl acetate/hexanes) to afford the title compound (16.8 g; 64%). MS(ES) m/z 203 [M+H].

b) 1-(3,4-Dimethylphenyl)-5-hydroxy-3-methyl-1H-pyrazole-4-carbaldehyde

Phosphorus oxychloride (4.82 mL, 51.6 mmol) was added dropwise to an ice-cooled, stirred suspension of 1-(3,4-dimethylphenyl)-3-methyl-3-pyrazolin-5-one (8.70 g, 43.0 mmol) in dimethylformamide (18.0 mL) at such a rate as to maintain the temperature below 20° C. After the addition, the mixture was heated at 100° C. for 2 h, then cooled, poured into iced water (200 mL). The resulting mixture was stirred for 18 h, then filtered. The solid was washed with water and dried to give the title compound (7.83 g, 79%) as a cream-coloured powder. MS (ES) m/e 231 [M+H]$^+$.

c) 3-(3-carboxyphenyl)-1-[(1-(3,4-dimethylphenyl)-5-hydroxy-3-methyl-1H-pyrazol-4-ylmethylene)amino]-2-thioxoimidazolidin-4-one Ethyl hydrazinoacetate hydrochloride (155 mg, 1.00 mmol) was added to a stirred solution of 3-isothiocyanatobenzoic acid (179 mg, 1.00 mmol) and di-isopropylethylamine (523 uL, 3.00 mmol) in dichloromethane (4 mL). The mixture was stirred for 96 h, evaporated under reduced pressure and partitioned between aqueous acetic acid and ethyl acetate. The organic extracts were washed with water, saturated aqueous sodium chloride, dried (magnesium sulfate) and evaporated under reduced pressure. The residue was chromatographed (silica gel, 5–15% methanol/ethyl acetate, then 20% methanol/ethyl acetate ±0.5% acetic acid) to give 1-amino-3-(3-carboxyphenyl)-2-thioxoimidazolidin-4-one (50 mg, 51%) contaminated with 6% uncyclised by-product, suitable for the next step. A solution of 1-amino-3-(3-carboxyphenyl)-2-thioxoimidazolidin-4-one (50 mg, 0.199 mmol) and 1-(3,4-dimethylphenyl)-5-hydroxy-3-methyl-1H-pyrazole-4-carbaldehyde (55 mg, 0.239 mmol) in ethanol/methanol (2:1, 15 mL) was allowed to stand a room temperature for 96 h. The solid was filtered off, washed with ether and dried to give the title compound (42 mg, 46%) as a powder. LCMS, m/e 464 [M+H]$^+$.

Example 3

3-(4-carboxyphenyl)-1-[(1-(3,4-dimethylphenyl)-5-hydroxy-3-methyl-1H-pyrazol-4-ylmethylene) amino]-2-thioxoimidazolidin-4-one The procedure of example 2(c) was followed here using 4-isothiocyanatobenzoic acid instead of 3-isothiocyanatobenzoic acid to give the title compound as a powder. LCMS, m/e 464 [M+H]$^+$.

Example 4

5-(4-carboxybenzylidene)-3-[(1-{3,4-dimethylphenyl}-4-hydroxy-3-methyl-1H-pyrazol-4-ylmethylene)amino]-2-thioxothiazolidin-4-one A mixture of 3-aminorhodanine (148 mg, 1.00 mmol), 1-(3,4-dimethylphenyl)-5-hydroxy-3-methyl-1H-pyrazole-4-carbaldehyde (230 mg, 1.00 mmol) and ethanol (10 mL) was stirred 96 h. The solid was filtered, washed with ethanol and ether and dried. A mixture of the resulting crude imine (80 mg, 0.222 mmol), piperidine (2 mg, 0.022 mmol), 4-formylbenzoic acid (33 mg, 0.222 mmol), benzoic acid (3 mg, 0.022 mmol) and toluene (10 mL) was heated under reflux for 6 h in an apparatus fitted with a Dean and Stark separator to remove water. After cooling, the solid was filtered off, washed with toluene and ether, and purified by reverse phase HPLC (CombiPrep ODS-A, 10–90% acetonitrile/water+0.1% trifluoroacetic acid) to give the title compound (18 mg, 16%) as a solid. LCMS, m/e 493 [M+H]$^+$.

Example 5

5-(3-carboxybenzylidene)-3-[(1-{3,4-dimethylphenyl}-4-hydroxy-3-methyl-1H-pyrazol-4-ylmethylene)amino]-2-thioxothiazolidin-4-one The procedure described in example 4 was followed here using 3-formylbenzoic acid instead of 4-formylbenzoic acid to give the title compound as a powder. LCMS, m/e 493 [M+H]$^+$.

Example 6

Capsule Composition

An oral dosage form for administering a presently invented agonist of the TPO receptor is produced by filing a standard two piece hard gelatin capsule with the ingredients in the proportions shown in Table I, below.

TABLE I

| INGREDIENTS | AMOUNTS |
|---|---|
| 3-[(2-hydroxy-3,5-dibromophen-1-yl)methyleneamino]-2-thioxothiazolidin-4-one (Compound A) | 25 mg |
| Lactose | 55 mg |
| Talc | 16 mg |
| Magnesium Stearate | 4 mg |

Example 7

Injectable Parenteral Composition

An injectable form for administering a presently invented agonist of the TPO receptor is produced by stirring 1.5% by weight of 3-[(2-hydroxy-3,5-dibromophen-1-yl)methyleneamino]-2-thioxothiazolidin-4-one (Compound A), monosodium salt (Compound 2) in 10% by volume propylene glycol in water.

Example 8

Tablet Composition

The sucrose, calcium sulfate dihydrate and a presently invented agonist of the TPO receptor, as shown in Table II below, are mixed and granulated in the proportions shown with a 10% gelatin solution. The wet granules are screened, dried, mixed with the starch, talc and stearic acid, screened and compressed into a tablet.

TABLE II

| INGREDIENTS | AMOUNTS |
|---|---|
| 3-[(2-hydroxy-3,5-dibromophen-1-yl)methyleneamino]-2-thioxothiazolidin-4-one (Compound A) | 20 mg |
| calcium sulfate dihydrate | 30 mg |
| sucrose | 4 mg |
| starch | 2 mg |
| talc | 1 mg |
| stearic acid | 0.5 mg |

While the preferred embodiments of the invention are illustrated by the above, it is to be understood that the invention is not limited to the precise instructions herein disclosed and that the right to all modifications coming within the scope of the following claims is reserved.

What is claimed is:

1. A method of treating of thrombocytopenia in a mammal in need thereof which comprises administering to such mammal a therapeutically effective amount of a compound of Formula (I):

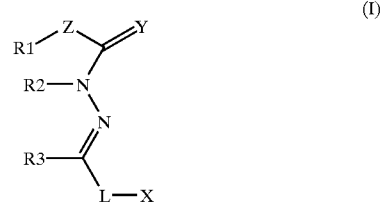

wherein:

$R^1$ and $R^2$ are each independently selected from hydrogen, $C_{1-12}$alkyl, aryl, substituted aryl, and alkyl substituted with one or more substituents selected from the group consisting of: alkoxy, acyloxy, aryl, substituted aryl, amino, N-acylamino, oxo, hydroxy, cycloalkyl, substituted cycloalkyl, —C(O)OR$^7$, —S(O)$_2$NR$^7$R$^8$, —S(O)$_n$R$^6$, aryloxy, nitro, cyano, halogen, and protected —OH, where $R^6$ is selected from hydrogen, alkyl, cycloalkyl, $C_1$–$C_{12}$aryl, substituted alkyl, substituted cycloalkyl and substituted $C_1$–$C_{12}$aryl, and $R^7$ and $R^8$ are independently selected from hydrogen, cycloalkyl, aryl, substituted cycloalkyl, substituted aryl, alkyl or alkyl substituted with one or more substituents selected from the group consisting of: alkoxy, acyloxy, aryloxy, amino, N-acylamino, oxo, hydroxy, —C(O)OR$^6$, —S(O)$_n$R$^6$, —C(O)NR$^6$R$^6$, —S(O)$_2$NR$^6$R$^6$, nitro, cyano, cycloalkyl, substituted cycloalkyl, halogen, $C_1$–$C_{12}$aryl, substituted $C_1$–$C_{12}$aryl and protected —OH where R$^6$ is as described above; and

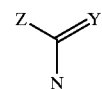

n is 0–3; or R$^1$ and R$^2$ taken together with the group to which they are attached represent a ring of formula (A):

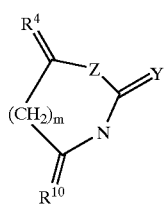

where
- $R^4$ and $R^{10}$ are each independently selected from two hydrogens, $=NR^5$, $=O$, $=S$, and $=CHR^5$, where $R^5$ is $C_1$–$C_{12}$aryl or substituted $C_1$–$C_{12}$aryl; and m is 0 to 2;
- Z is a bond or selected from S or $NR^5$, where $R^5$ is $C_1$–$C_{12}$aryl or substituted $C_1$–$C_{12}$aryl;
- $R^3$ is selected from hydrogen, $C_1$–$C_{10}$alkyl, phenyl, substituted phenyl, carboxyl or $C_1$–$C_{10}$alkoxycarbonyl;
- L is a group of formula (L):

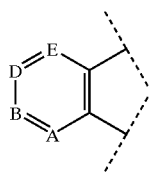

where
- A, B, D and E independently represent $CR^{11}$ or N; where $R^{11}$ is selected from hydrogen, halogen, $-CF_3$, $-CN$, $-SO_3H$, $-SO_3Na$, $-SO_2R^{14}$, $-NO_2$, phenyl, substituted phenyl, $C_1$–$C_{10}$alkyl, $C_1$–$C_{10}$alkoxy, $C_1$–$C_{10}$acyloxy, arylalkoxy, $-COR^{14}$, $-NR^{12}R^{13}$, hydroxy or cycloalkyl;
   where $R^{14}$ is selected from hydroxy, $C_1$–$C_{10}$alkyl, phenyl, amino, mono- or dialkylamino;
- $R^{12}$ and $R^{13}$ are independently selected from hydrogen, $C_{1-10}$alkyl, $C_1$–$C_{12}$aryl, substituted $C_1$–$C_{12}$aryl, $C_{1-10}$acyl or cycloalkyl;
- or either $A=B$ or $D=E$ alternatively represent O, S or $NR^{12}$; where $R^{12}$ is as defined above;
- Y is selected from S, O and $NR^{15}$, where $R^{15}$ is selected from hydrogen, $C_1$–$C_{10}$alkyl, substituted $C_1$–$C_{10}$alkyl, $C_1$–$C_6$alkylphenyl, substituted $C_1$–$C_6$alkylphenyl, $C_1$–$C_{10}$acyl, substituted $C_1$–$C_{10}$acyl, or $SO_2R^9$, where $R^9$ is $C_1$–$C_{10}$alkyl, substituted $C_1$–$C_{10}$alkyl, $C_1$–$C_{12}$aryl or substituted $C_1$–$C_{12}$aryl; and
- X is selected from $SR^{16}$, $OR^{16}$ or $NHR^{17}$; where $R^{16}$ is hydrogen, $C_1$–$C_{10}$alkyl or substituted $C_1$–$C_{10}$alkyl;
- $R^{17}$ is hydrogen, $C_1$–$C_{10}$alkyl, substituted $C_1$–$C_{10}$alkyl, $C_1$–$C_6$alkylphenyl, $C_1$–$C_{10}$acyl, substituted $C_1$–$C_{10}$acyl or $SO_2R^9$; where $R^9$ is $C_1$–$C_{10}$alkyl, substituted $C_1$–$C_{10}$alkyl, $C_1$–$C_{12}$aryl or substituted $C_1$–$C_{12}$aryl; or a pharmaceutically acceptable salt, hydrate, solvate or ester thereof, provided that;
- when $R^1$ and $R^2$ do not form a ring and X is not $-NHSO_2R^9$, $R^5$ is not a substituted or unsubstituted pyridyl or a substituted or unsubstituted phenyl.

2. The method of claim 1 wherein the compound is selected form:

3-[(2-hydroxy-3,5-dibromophen-1-yl)methyleneamino]-2-thioxothiazolidin-4-one;
3-(3-carboxyphenyl)-1-[(1-(3,4-dimethylphenyl)-5-hydroxy-3-methyl-1H-pyrazol-4-ylmethylene)amino]-2-thioxoimidazolidin-4-one;
3-(4-carboxyphenyl)-1-[(1-(3,4-dimethylphenyl)-5-hydroxy-3-methyl-1H-pyrazol-4-ylmethylene)amino]-2-thioxoimidazolidin-4-one;
5-(4-carboxybenzylidene)-3-[(1-{3,4-dimethylphenyl}-4-hydroxy-3-methyl-1H -pyrazol-4-ylmethylene)amino]-2-thioxothiazolidin-4-one; and
5-(3-carboxybenzylidene)-3-[(1-{3,4-dimethylphenyl}-4-hydroxy-3-methyl-1H -pyrazol-4-ylmethylene)amino]-2-thioxothiazolidin-4-one;

or a pharmaceutically acceptable salt, hydrate, solvate or ester thereof.

3. A method of enhancing platelet production in a mammal, including a human, in need thereof which comprises administering to such mammal a therapeutically effective amount of a compound of Formula (I) as defined in claim 1.

4. The method of claim 3 wherein the compound is selected from:

3-[(2-hydroxy-3,5-dibromophen-1-yl)methyleneamino]-2-thioxothiazolidin-4-one;
3-(3-carboxyphenyl)-1-[(1-(3,4-dimethylphenyl)-5-hydroxy-3-methyl-1H-pyrazol-4-ylmethylene)amino]-2-thioxoimidazolidin-4-one;
3-(4-carboxyphenyl)-1-[(1-(3,4-dimethylphenyl)-5-hydroxy-3-methyl-1H -pyrazol-4-ylmethylene)amino]-2-thioxoimidazolidin-4-one;
5-(4-carboxybenzylidene)-3-[(1-{3,4-dimethylphenyl}-4-hydroxy-3-methyl-1H -pyrazol-4-ylmethylene)amino]-2-thioxothiazolidin-4-one; and
5-(3-carboxybenzylidene)-3-[(1-{3,4-dimethylphenyl}-4-hydroxy-3-methyl-1H -pyrazol-4-ylmethylene)amino]-2-thioxothiazolidin-4-one;

or a pharmaceutically acceptable salt, hydrate, solvate or ester thereof.

5. The method of claim 1 wherein the compound is administered orally.

6. The method of claim 1 wherein the compound is administered parenterally.

7. A method of agonizing the thrombopoietin receptor in a subject which comprises administering an effective amount of a compound of Formula (I), as defined in claim 1.

8. The method of claim 1 wherein the compound is

3-[(2-hydroxy-3,5-dibromophen-1-yl)methyleneamino]-2-thioxothiazolidin-4-one;

or a pharmaceutically acceptable salt, hydrate, solvate or ester thereof.

9. A compound selected from:

3-[(2-hydroxy-3,5-dibromophen-1-yl)methyleneamino]-2-thioxothiazolidin-4-one;
3-(3-carboxyphenyl)-1-[(1-(3,4-dimethylphenyl)-5-hydroxy-3-methyl-1H-pyrazol-4-ylmethylene)amino]-2-thioxoimidazolidin-4-one;
3-(4-carboxyphenyl)-1-[(1-(3,4-dimethylphenyl)-5-hydroxy-3-methyl-1H-pyrazol-4-ylmethylene)amino]-2-thioxoimidazolidin-4-one;

5-(4-carboxybenzylidene)-3-[(1-{3,4-dimethylphenyl}-4-hydroxy-3-methyl-1H-pyrazol-4-ylmethylene)amino]-2-thioxothiazolidin-4-one; and 5-(3-carboxybenzylidene)-3-[(1-{3,4-dimethylphenyl}-4-hydroxy-3-methyl-1H-pyrazol-4-ylmethylene)amino]-2-thioxothiazolidin-4-one;

or a pharmaceutically acceptable salt, hydrate, solvate or ester thereof.

10. A pharmaceutical composition comprising a compound according to claim 1, and a pharmaceutically acceptable carrier.

11. The method of claim 1 in which the mammal is a human.

* * * * *